United States Patent
Zhou et al.

(10) Patent No.: US 7,286,234 B2
(45) Date of Patent: Oct. 23, 2007

(54) COPPER FOIL INSPECTION DEVICE COPPER FOIL INSPECTION METHOD DEFECT INSPECTION DEVICE AND DEFEAT INSPECTION METHOD

(75) Inventors: Qing Wei Zhou, Tokyo (JP); Jun Fujiwara, Tokyo (JP); Koji Yamabe, Saitama (JP); Ayumu Inoue, Saitama (JP)

(73) Assignees: Kokusai Gijutsu Kaihatsu Co. Ltd., Tokyo (JP); Mitsui Mining & Smelting Co. Ltd., Tokyo (JP)

( * ) Notice: Subject to any disclaimer, the term of this patent is extended or adjusted under 35 U.S.C. 154(b) by 428 days.

(21) Appl. No.: 10/498,695

(22) PCT Filed: Dec. 12, 2002

(86) PCT No.: PCT/JP02/13000

§ 371 (c)(1),
(2), (4) Date: Jul. 29, 2004

(87) PCT Pub. No.: WO03/054530

PCT Pub. Date: Jul. 3, 2003

(65) Prior Publication Data

US 2006/0109466 A1 May 25, 2006

(30) Foreign Application Priority Data

Dec. 13, 2001 (JP) .............................. 2001-380380

(51) Int. Cl.
*G01N 21/84* (2006.01)
(52) U.S. Cl. ..................................... 356/430; 356/237.1
(58) Field of Classification Search ................ 356/430, 356/237.1
See application file for complete search history.

(56) References Cited

U.S. PATENT DOCUMENTS 4,030,830 A * 6/1977 Holly .......................... 356/489

FOREIGN PATENT DOCUMENTS

| JP | 58-204353 | 11/1983 |
|----|-----------|---------|
| JP | 60-228943 | 11/1985 |
| JP | 07-306157 | 11/1995 |
| JP | 08-178867 | 7/1996 |
| JP | 10-325809 | 12/1998 |
| JP | 11-295241 | 10/1999 |
| JP | 2000-028536 | 1/2000 |
| JP | 2001-056297 | 2/2001 |
| JP | 2001-108639 | 4/2001 |

OTHER PUBLICATIONS

International Search Report dated Apr. 1, 2003, Appl. No. PCT/JP02/13000.

* cited by examiner

*Primary Examiner*—Roy M. Punnoose
(74) *Attorney, Agent, or Firm*—McCracken & Frank LLP (57) ABSTRACT

A surface of copper foil wound onto a guide roller 26 is irradiated with light. Specular light from the copper foil surface is received by CCD cameras 14a, and scattered light from the copper foil surface is received by CCD cameras 14b. When, in a region in which the amount of specular light received by the CCD cameras 14a is equal to or larger than a first threshold, a portion having a luminance equal to or larger than a second threshold is present, and when the amount of scattered light received by the CCD cameras 14b is smaller than a luminance average, that region is determined to be a defective copper portion.

10 Claims, 9 Drawing Sheets

COPPER FOIL INSPECTION DEVICE COPPER FOIL INSPECTION METHOD DEFECT INSPECTION DEVICE AND DEFEAT INSPECTION METHOD

TECHNICAL FIELD

The present invention relates to a copper foil inspection apparatus and a copper foil inspection process, in which a surface of copper foil used as a printed board for an electronic circuit is irradiated with light in order to optically detect a defective copper portion which is likely to remain after etching of the printed board, and to a defect inspection apparatus and a defect inspection process for specifying a defective portion of a sheet-like object to be inspected.

BACKGROUND ART

A variety of surface flaw inspection techniques, in which a flaw in a surface of an object to be inspected, such as a surface of a thin steel sheet, is optically detected by irradiating the surface with light and analyzing light reflected from the surface, have been proposed.

For example, Japanese Patent Application Laid-Open (JP-A) No. 58-204353 proposes a process for detecting a flaw in a surface of a metal body, wherein a surface of an object to be inspected is irradiated with light, and specular light and diffused light reflected from the surface are detected by cameras. In this surface flaw detection process, light is made incident on the surface of the object to be inspected at an angle of 35° to 75°, and light reflected from the surface is received by two cameras, which are disposed in a direction in which specular light advances and a direction which is within 20° from the direction in which the incident light or the specular light advances. Subsequently, signals generated by the two cameras at the time of receiving light are compared with each other by, for example, obtaining a logical sum thereof. Only when the cameras detect an abnormal value at the same time, a portion having the abnormal value is regarded as a flaw. In this way, the surface flaw detection process which is not affected by noise is realized.

Further, JP-A No. 60-228943 proposes a process for inspecting a flaw in a surface of an object to be inspected by receiving backscattering light from the test substance. In this flaw inspection process, a flaw in a surface of a stainless steel sheet is detected by making light incident onto the stainless steel sheet at a large incidence angle and detecting light reflecting back, namely, backscattering light.

Moreover, JP-A No. 8-178867 proposes an apparatus for detecting a flaw in hot-rolled flat steel by detecting a plurality of reflected backscattering light beams. This hot-rolled flat steel flaw detection apparatus detects a scratch on the hot-rolled flat steel. In this flaw detection apparatus, the angle of a slope of a scratch is 10 to 40°, and plural cameras are disposed in directions in which reflected backscattering light beams advance, so as to receive all the specular light reflected from the slope of the scratch having an angle within the above range.

However, the purpose of the measuring techniques proposed above is to detect a remarkably irregular flaw. It has been difficult to reliably detect a flaw which is formed by adhesion on copper foil and not remarkably irregular.

For example, as for the flaw detection process disclosed in JP-A No. 58-204353, the two cameras for receiving specular light and scattered light are provided so that the influence of noise is removed by obtaining a logical sum of the detection signals generated by the cameras. Thus, the process can be used to detect remarkably irregular flaws, namely, flaws in the surface which are cracked, dug up or turned up because signals of these flaws can be picked up by both the cameras. However, it is impossible to reliably detect flaws which are not so remarkably irregular that only one of the cameras can pick up signals thereof.

Further, the surface condition inspection process disclosed in JP-A No. 60-228943 is intended to detect raised flaws, which are conspicuous on the stainless steel sheet having small surface roughness. Thus, this process cannot be used for defects which do not have conspicuously raised portions.

Furthermore, the apparatus for detecting a flaw in hot-rolled flat steel disclosed in JP-A No. 8-178867 is intended to detect scratches, and the detection is based on the capture of specular light reflected from the slope of a scratch. Thus, reflected backscattering light of some of the defects which are not remarkably irregular may not be captured by the apparatus.

In view of the above drawbacks, an object of the present invention is to provide a defect inspection apparatus and a defect inspection process for detecting with high accuracy a defect of an object to be inspected. Particularly, an object of the present invention is to provide a copper foil inspection apparatus and a copper foil inspection process for detecting with high accuracy a defective copper portion of a surface of copper foil, which portion is likely to remain after etching.

DISCLOSURE OF THE INVENTION

In order to achieve the above objects, a first aspect of the present invention is a copper foil inspection apparatus comprising: a light source for irradiating a surface of copper foil with light; first light-receiving means for receiving specular light from the copper foil surface; second light-receiving means for receiving scattered light from the copper foil surface; and a determining portion which, when an amount of light received from a predetermined region of the copper foil surface by the first light-receiving means is no less than a first threshold and an amount of light received from the predetermined region by the second light-receiving means is no more than a second threshold which is smaller than the first threshold, determines that the predetermined region is a defective copper portion.

Further, a second aspect of the present invention is a copper foil inspection process comprising: irradiating a surface of a copper foil with light; receiving specular light from the copper foil surface by first light-receiving means; receiving scattered light from the copper foil surface by second light-receiving means; and determining, when an amount of light received from a predetermined region of the copper foil surface by the first light-receiving means is no less than a first threshold and an amount of light received from the predetermined region by the second light-receiving means is no more than a second threshold which is smaller than the first threshold, that the predetermined region is a defective copper portion.

Copper foil is generally manufactured by an electrolyzing step for precipitating copper foil and a roughening step for further adhering copper powder on a surface of the precipitated copper foil. Research by the present inventors has revealed that the following portions of the copper foil precipitated in the electrolyzing step are likely to remain on the printed board after etching: a portion which conspicuously protrudes from the copper foil surface as compared with other portions of the surface, or has a large protruding area (hereinafter collectively referred to as the "irregularly precipitated portions"); and a portion formed such that a relatively large piece of copper is deposited in the roughening step on a portion of the copper foil surface which has been precipitated very finely in the electrolyzing step (hereinafter collectively referred to as the "copper powder portions"). Thus, in the present invention, the irregularly precipitated portions and the copper powder portions which are likely to remain after etching (hereinafter referred to as the "defective copper portions") are detected as defective portions.

According to the first and second aspects of the present invention, the copper foil surface is irradiated with light, specular light from the predetermined region of the copper foil surface is received by the first light-receiving means, and scattered light from the predetermined region is received by the second light-receiving means. It has become clear by experiment that the amount of specular light from a defective copper portion of the copper foil surface is larger than the amount of specular light from a non-defective copper portion, and that the amount of scattered light from a defective copper portion of the surface of an object to be inspected is smaller than the amount of scattered light from a non-defective copper portion. However, since a direction in which reflected light advances may be changed by a flaw or the like on the copper foil surface, it is difficult to accurately determine the presence of a defective copper portion when the determination is made based on either the amount of reflected light or the amount of scattered light. Therefore, a threshold is set for the determining portion in order to determine the presence of a defective copper portion. When the predetermined region exists in which the amount of light received by the first light-receiving means is no less than the first threshold and the amount of light received by the second light-receiving means is no more than the second threshold, the determining portion determines that the predetermined region is a defective copper portion.

As described above, the threshold is set based on the reflection property of light reflected from a defective copper portion adhering to the copper foil surface, and the presence or absence of a defective copper portion is determined based on comparison of the results of the two types of light received, i.e., specular light and scattered light, with the respective thresholds. Thus, as compared with a case in which the determination is made based on either reflected light or scattered light, a defect caused by adhesion of the defective copper portion can be extracted more accurately.

In the first and second aspects of the present invention, the predetermined region can also be determined to be a defective copper portion when the predetermined region includes an area, from which an amount of light received by the first light-receiving means is no less than a third threshold which is larger than the first threshold.

As described above, the two thresholds are set for the specular light received, and the presence of the area, from which the amount of light received is no less than the third threshold, in the predetermined region, from which the amount of light received is no less than the first threshold, is added as a condition for the determination of a defective copper portion. In this way, the defective copper portion can be detected more accurately.

Moreover, in the first and second aspects of the present invention, the predetermined region can also be determined to be a defective copper portion when the size of the predetermined region is no less than a predetermined size. When the defective copper portion is smaller than the predetermined size, the defective copper portion is often not affected by etching. Further, a portion having an abnormal value caused by noise also needs to be removed. When a region of size equal to or larger than the predetermined size is formed by the predetermined regions each satisfying the condition that the amount of light received therefrom is no less than the first threshold, that region is determined to be a defective copper portion. As a result, a portion which is not affected by etching and a portion having an abnormal value caused by noise can be removed. Thus, the defective copper portion can be extracted more accurately.

The second light-receiving means according to the first and second aspects can receive appropriate scattered light by receiving scattered light from the front of the surface of the object to be inspected.

In the first and second aspects of the present invention, a defective copper portion can be determined with higher accuracy as follows. Light reflected from the predetermined region which has been determined to be a defective copper portion is received by third light-receiving means of resolution higher than that of the first and second light-receiving means. The determining portion further distinguishes the presence or absence of the defective copper portion based on the amount of light received by the third light-receiving means, and determines that the predetermined region is the defective copper portion when the determining portion distinguishes the presence of the defective copper portion. As a result, the defective copper portion can be determined with higher accuracy.

A third aspect of the present invention is a defect inspection apparatus comprising: first image pickup means for picking up an image of a surface of a moving, sheet-like object to be inspected, at an upstream side in a direction in which the object to be inspected is moved; detecting means for detecting a defective portion of the surface of the object to be inspected based on the image which has been picked up; second image pickup means for picking up an image of the defective portion at a downstream side in the direction in which the object to be inspected is moved, the second image pickup means having a resolution higher than that of the first image pickup means; and defect determining means for determining, when a defect is verified in the defective portion based on the image picked up by the second image pickup means, that the defect is present in the defective portion.

Further, a fourth aspect of the present invention is a defect inspection process comprising: picking up, by first image pickup means, an image of a surface of a moving, sheet-like object to be inspected, at an upstream side in a direction in which the object to be inspected is moved; detecting a defective portion of the surface of the object to be inspected based on the image which has been picked up; picking up, by second image pickup means, an image of the defective portion at a downstream side in the direction in which the object to be inspected is moved, the second image pickup means having a resolution higher than that of the first image pickup means; and determining, when a defect is verified in the defective portion based on the image picked up by the second image pickup means, that the defect is present in the defective portion.

According to the third and fourth aspects of the present invention, a defective portion is detected by the first image pickup means of low resolution which picks up an image of the surface of the sheet-like object to be inspected. Another image of the detected defective portion is picked up by the second image pickup means having a resolution higher than that of the first image pickup means. When a defect is verified based on the image picked up by the second image pickup means, it is determined that a defect is present in the defective portion. Therefore, defects can be detected with higher accuracy.

Further, only the image of a portion which is determined to be defective based on the image picked up by the first image pickup means is picked up by the expensive, high-resolution image pickup means. Thus, an image pickup range can be limited, and a defect of the object to be inspected can be effectively detected.

BEST MODE FOR CARRYING OUT THE INVENTION

A copper foil inspection apparatus of the present invention will be described in detail below with reference to the drawings.

FIRST EMBODIMENT

Figure 1:
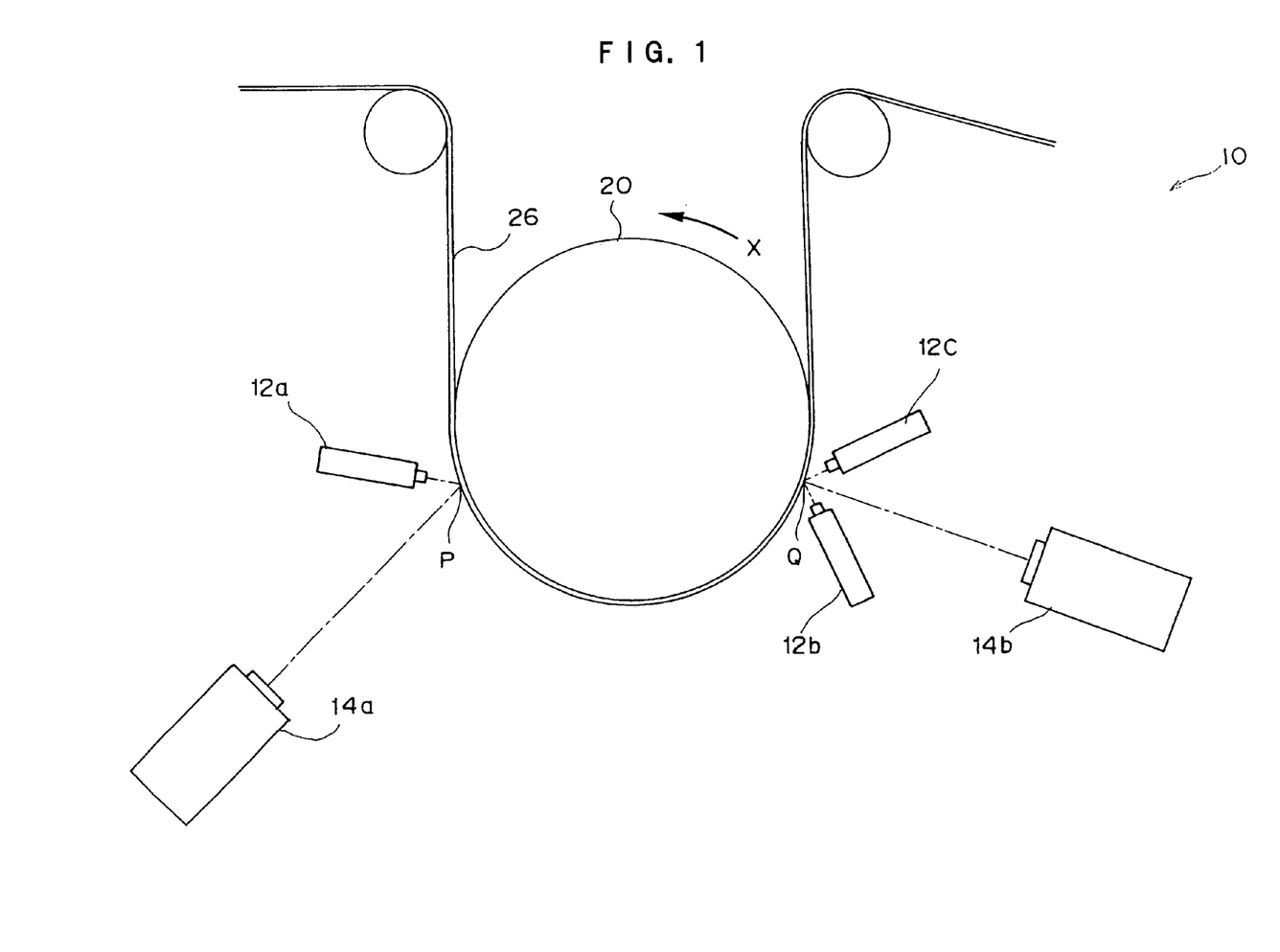
FIG. 1 is a schematic structural diagram of a part of a copper foil inspection apparatus according to an embodiment of the present invention.

A copper foil inspection apparatus 10 according to the present embodiment includes, as shown in FIG. 1, light sources 12a, 12b and 12c, CCD sensors 14a and 14b, a guide roller 20, and a signal processing section 28 (not shown in FIG. 1).

Copper foil 26 as an object to be inspected is taken out from an unillustrated copper foil manufacturing apparatus and guided via a plurality of rollers to the copper foil inspection apparatus 10. Copper foil having, for example, a width of 1300 mm or 1350 mm and a thickness of 12 μm, 18 μm, 35 μm or 70 μm is used as the copper foil 26. The guide roller 20 is rotated in a direction of arrow X to convey the copper foil 26 as the object to be inspected. The copper foil 26 is wound along the circumference of a lower portion of the guide roller 20 with the surface thereof on the outer side.

The light source 12a is disposed so as to irradiate a reading portion P of the copper foil 26 with light (at an incidence angle of, for example, 30°). The reading portion P is located at a position lower than a central portion of the guide roller 20 in a horizontal direction thereof. The multiple (for example, six) CCD sensors 14a are disposed along an axial direction of the guide roller 20 and on an optical axis of specular light reflected from the reading portion P which is irradiated with the light source 12a. The CCD sensors 14a receive the light reflected from the reading portion P.

An unillustrated rotary encoder 16 for outputting a pulse signal in accordance with the rotation of the guide roller 20 is connected to a rotary shaft of the guide roller 20.

The light source 12b is disposed so as to irradiate a reading portion Q of the copper foil 26 with light (at an incidence angle of, for example, 45°) The reading portion Q is located at a position lower than the central portion of the guide roller 20 in the horizontal direction thereof. Further, the light source 12c is disposed at a position opposite the position of the light 12b with respect to a normal line of the reading portion Q, and irradiates the reading portion Q with light. The multiple (e.g., six) CCD sensors 14b are disposed along the axial direction of the guide roller 20 and in the direction of the normal line of the reading portion Q, and receive scattered light from the reading portion Q.

Figure 2:
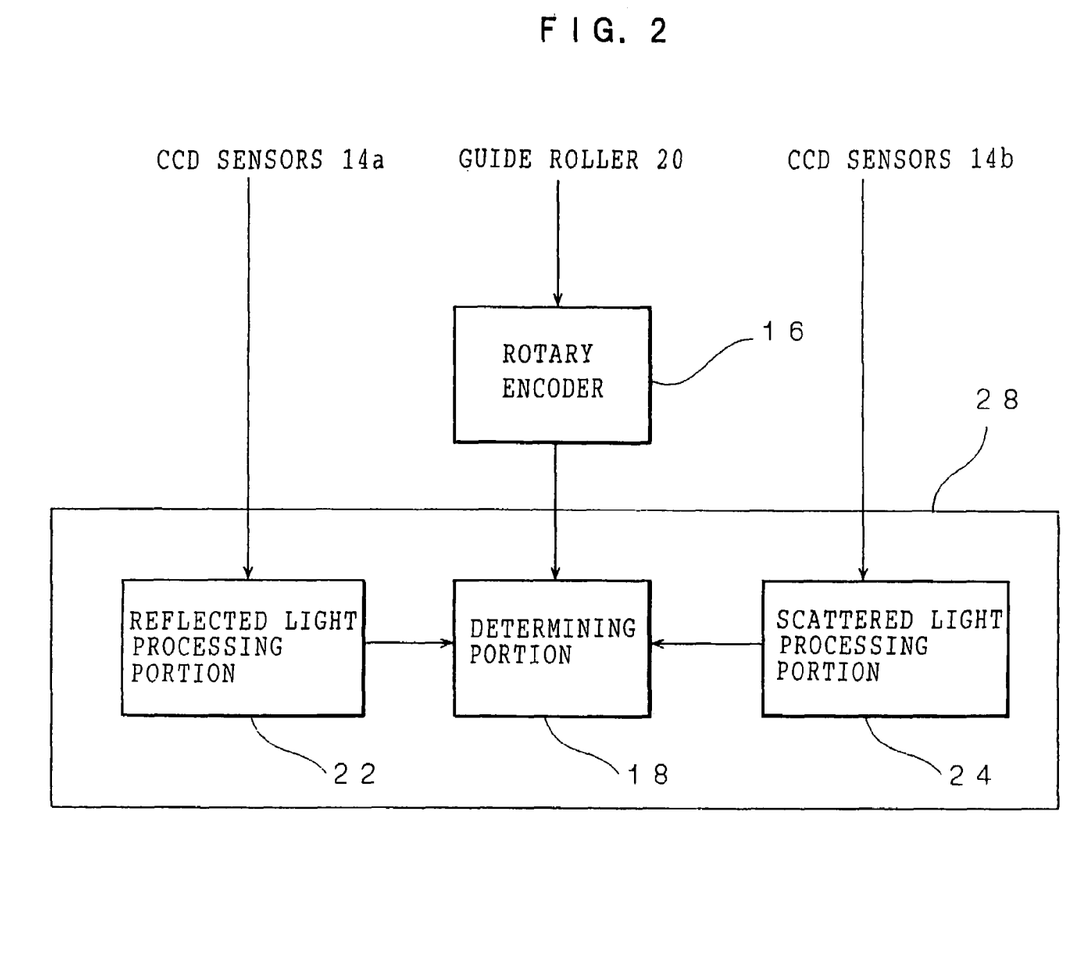
FIG. 2 is a schematic block diagram of a signal processing section according to a first embodiment.

As shown in FIG. 2, the signal processing section 28 includes a determining portion 18, a reflected light processing portion 22, and a scattered light processing portion 24. The reflected light processing portion 22 is connected to the CCD sensors 14a and the determining portion 18, while the scattered light processing portion 24 is connected to the CCD sensors 14b and the determining portion 18. The rotary encoder 16 is connected to the guide roller 20 and the determining portion 18. Each of the reflected light processing portion 22, the scattered light processing portion 24, and the determining portion 18 can be formed by a microcomputer including a CPU, a ROM and a RAM.

Operation of the present embodiment will be described next.

Figure 3A:
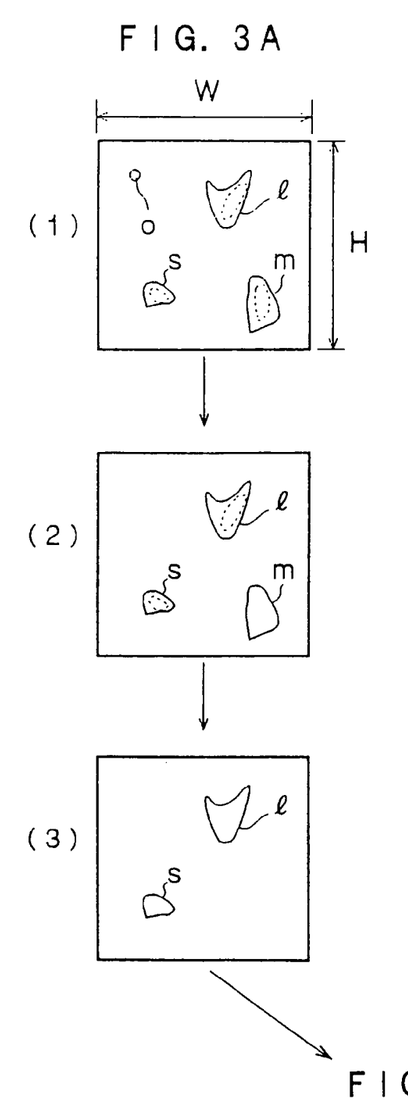
FIGS. 3A through 3C show examples of an image read by CCD sensors.

When an instruction to start up the copper foil inspection apparatus 10 is given to an unillustrated driving portion, the guide roller 20 is rotated in the direction of X, thereby starting conveyance of the copper foil 26. At the same time, the light source 12a irradiates the reading portion P of the copper foil 26 with light at an incidence angle of, for example, 30°, and the CCD sensors 14a receive light reflected from the reading portion P of the copper foil 26 and advancing diagonally from the reading portion P, namely, specular light, at a light-receiving angle of 30°. The light sources 12b and 12c irradiate the reading portion Q of the copper foil 26 with light at an incidence angle of, for example, 45°, and the CCD sensors 14b receive scattered light from the reading portion Q at the front thereof, namely, at a light-receiving angle of 0°. As shown in FIG. 3A, light is received in predetermined units of the width W and the length H of the copper foil 26. The CCD sensors 14a and 14b transmit to the reflected light processing portion 22 and the scattered light processing portion 24 image data obtained by converting each pixel into an 8-bit luminance signal in accordance with the intensity of the light received.

Figure 4:
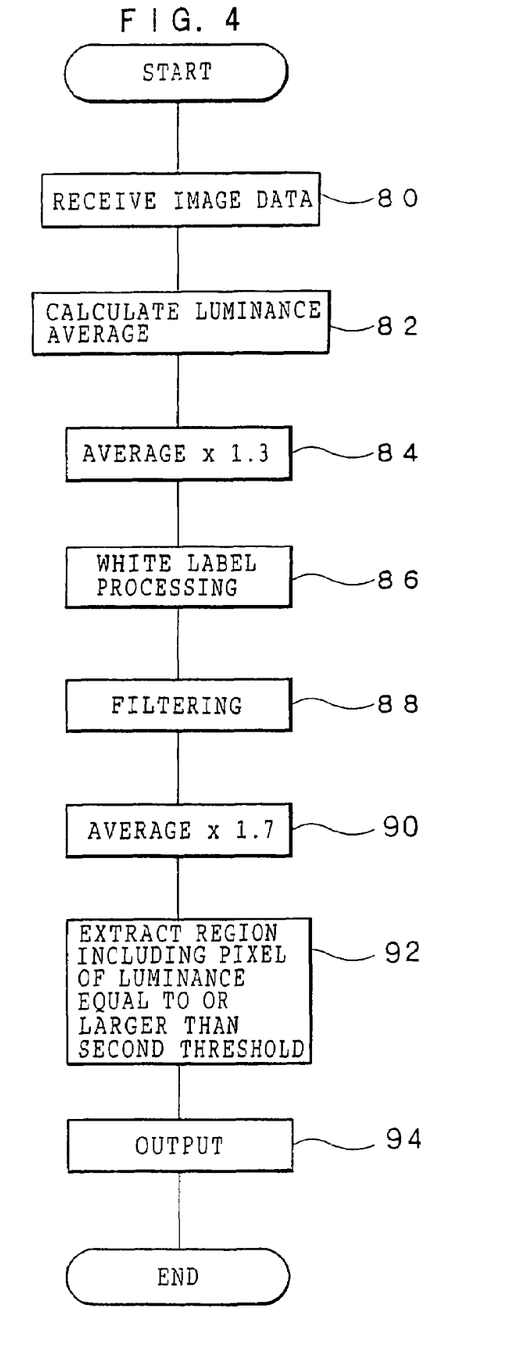
FIG. 4 is a flowchart of a process for reflected light.

Upon receiving the image data from the CCD sensor 14a, the reflected light processing portion 22 executes a process for reflected light shown in FIG. 4.

Image data is received in step 80, and an average of the luminance of the image data received is calculated in step 82. In step 84, the luminance average calculated is multiplied by, for example, 1.3. In this way, a first value which is obtained by multiplying the luminance average by a predetermined value is used as a first threshold.

It has become clear by experiments that a defective copper portion of the copper foil 26 has a larger amount of reflected light than a non-defective portion of the copper foil surface. Namely, a defective copper portion has a luminance higher than that of a non-defective copper portion, and looks whitish to the human eye. Thus, in the image data received, a portion having high luminance is likely to be a defective copper portion.

For this reason, in step 86, a white label processing is carried out for each region formed by pixels of luminance larger than the value obtained by multiplying the luminance average by 1.3, when the first threshold is, for example, 1.3 times the calculated luminance average. The white-labeled region indicates a region of high luminance. In step 88, a somewhat large white-labeled region, namely, a somewhat large region formed by white-labeled pixels, is extracted. Since some noise is generated in the image data converted by the CCD sensors 14*a*, a pixel of high luminance may be formed by the noise and erroneously labeled white even when this pixel does not form a defective copper portion. Further, the irregularly precipitated portions or copper powder portions which are small and not affected by etching may be formed on the copper foil. Thus, this processing is intended to remove noise and these small portions. Specifically, filtering for extracting only white-labeled regions of the predetermined size or larger is performed, such that white-labeled regions smaller than the predetermined size are removed. The predetermined size is set in view of the accuracy of the CCD sensors 14*a*, and the size of the irregularly precipitated portions or copper powder portions, which should be removed as defects.

In the image picked up by the CCD sensors 14*a*, when a pixel having a luminance of a predetermined value or more is present among the pixels forming the white-labeled region of the predetermined size or larger, namely, when, in a region of somewhat high luminance, there is a portion of higher luminance, there is a high possibility that etching residue will be formed. Thus, in step 90, a luminance which is, for example, 1.7 times the luminance average is determined. The luminance which is 1.7 times the luminance average, namely, a second value which is obtained by multiplying the luminance average by a predetermined value and is larger than the first value obtained by multiplying the luminance average by a predetermined value is used as a second threshold. In step 92, only a white-labeled region, in which a pixel of luminance larger than the second threshold is present among the white-labeled pixels forming the labeled region of the predetermined size or larger, is extracted, and a white-labeled region having no pixel of luminance larger than the second threshold is excluded. Labeling and filtering may also be carried out for pixels of luminance larger than the second threshold in the same way as described above, and only a region of predetermined size or larger may be used as an object of determination. Subsequently, in step 94, the image subjected to the white label processing is outputted to the determining portion 18, and this process ends.

An example of the image picked up by the CCD sensors 14*a*, an example of the image obtained after step 88 in the process for reflected light, and an example of the image obtained after the process for reflected light are illustrated in (1), (2) and (3) in FIG. 3A, respectively. In the image data picked up by the CCD sensors 14*a*, 1, m, s and o are recognized as portions having a luminance larger than the value obtained by multiplying the average by 1.3 ((1)). However, after step 88, the portion o which is smaller than the predetermined size is removed, and the portions l, s and m remain ((2)). After the process ends, the portion m having no pixels of luminance larger than the value obtained by multiplying the average by 1.7 is removed, and the portions l and m are extracted ((3)). These portions are estimated to be defective portions.

According to the process for reflected light, a region, in which a portion having a luminance equal to or larger than the second value obtained by multiplying the luminance average by a predetermined value is present among the portions which are equal to or larger than the first value obtained by multiplying the luminance average by a predetermined value and are equal to or larger than the predetermined size, is extracted.

Figure 5:
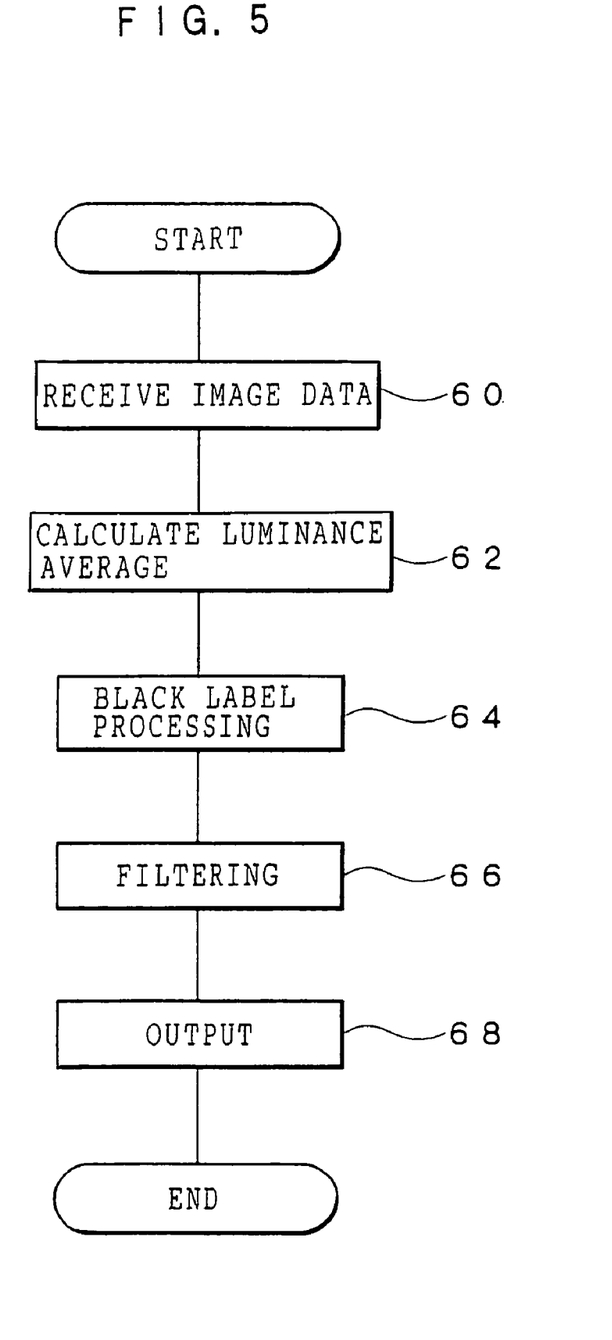
FIG. 5 is a flowchart of a process for scattered light.

The scattered light processing portion 24 executes a process for scattered light shown in FIG. 5 upon receiving the image data from the CCD sensors 14*b*.

The image data is received in step 60, and an average of the luminance of the image data received is calculated in step 62. The luminance average of the image data can be calculated by dividing by the number of pixels the total of the luminance of all pixels within an area defined by the width W and the length H of the copper foil 26.

It has become clear by experiments that a defective portion of the copper foil 26 has a smaller amount of scattered light than a non-defective portion of the copper foil surface. Namely, a defective copper portion has a luminance lower than that of a non-defective copper portion, and looks dark to the human eye. Thus, in the image data received, a portion having low luminance is likely to be a defective copper portion. For this reason, in step 64, a black label processing is carried out for each region formed by pixels of luminance smaller than the calculated luminance average, which is used as a threshold. In step 66, a black-labeled region of predetermined size or larger, namely, a somewhat large region formed by black-labeled pixels, is extracted. Since some noise is generated in the image data converted by the CCD sensors 14*b*, a pixel of low luminance may be formed by the noise and erroneously labeled black even when this pixel does not form a defective copper portion. Further, the irregularly precipitated portions or copper powder portions which are small and not affected by etching may be formed on the copper foil. Thus, this processing is intended to remove noise and these small portions. Specifically, filtering for extracting only black-labeled regions of the predetermined size or larger is performed, such that black-labeled regions smaller than the predetermined size are removed. In step 68, the image subjected to the black label processing is outputted to the determining portion 18, and this process ends.

While the luminance average of each image received is used as the threshold in the above description, other thresholds may be set and used to detect a defective copper portion. Further, the above-described predetermined size is set in view of the accuracy of the CCD sensors 14*b*, and the size of defective copper portions, which should be removed as defects.

Figure 3B:
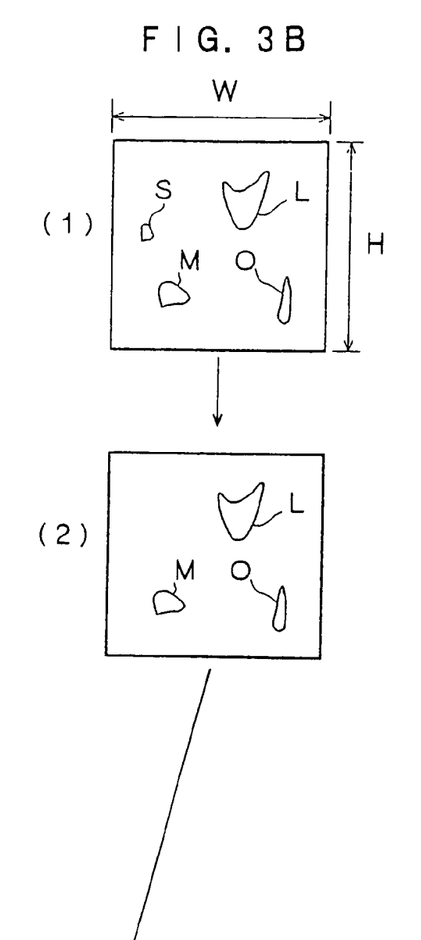

An example of the image picked up by the CCD sensors 14*b*, and an example of the image obtained after the process for scattered light are illustrated in (1) and (2) in FIG. 3B, respectively. In the image data picked up by the CCD sensors 14*b*, L, M, S and O are recognized as portions having a luminance smaller than the average. The portion S which is smaller than the predetermined size is removed by this process, and the portions L, M and O are estimated to be defective portions.

According to the process for scattered light, a portion which has a low luminance and is equal to or larger than the predetermined size can be extracted.

Figure 6:
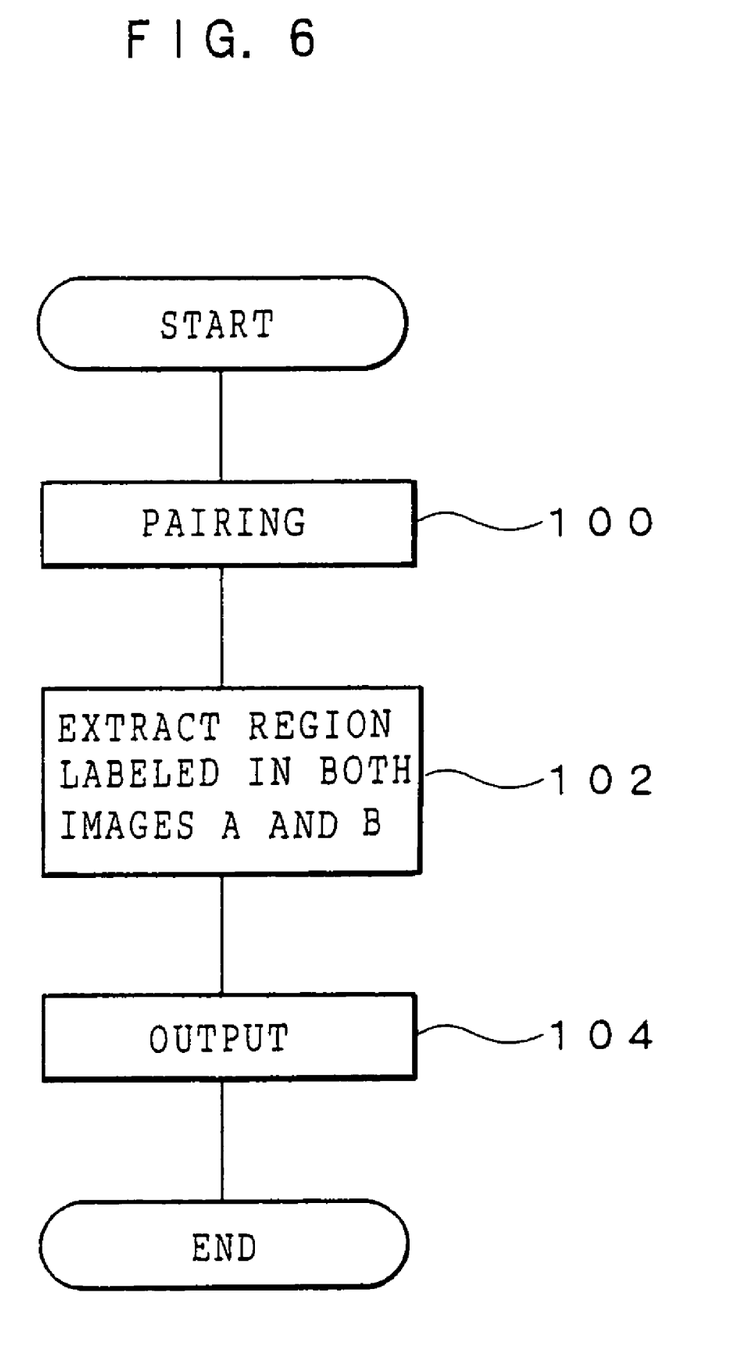
FIG. 6 is a flowchart of a determination process.

The determining portion 18 receives image data A and image data B from the reflected light processing portion 22 and the scattered light processing portion 24, respectively, and executes a process for extracting a defective portion of the copper foil 26.

The copper foil 26 is conveyed by the guide roller 20 and read at the reading positions P and Q by the CCD sensors 14a and 14b, respectively. Thus, a difference exists in the time at which an identical portion of the copper foil 26 is read by the CCD sensors 14a and 14b. Therefore, in step 100, the time interval is measured by counting pulse signals which are obtained by the rotary encoder 16 and correspond to the rotational speed of the guide roller 20, the image data B which is received after the image data A at this predetermined time interval is determined as the image data for the identical portion of the copper foil 26, and then pairing of the image data A and the image data B for the identical portion of the copper foil 26 is carried out. In step 102, the paired image data A and image data B are compared with each other, and a region which has been labeled black in the image data A and labeled white in the image data B is extracted as a defective copper portion. In step 104, the extracted portion is outputted, and the process ends.

Figure 3C:
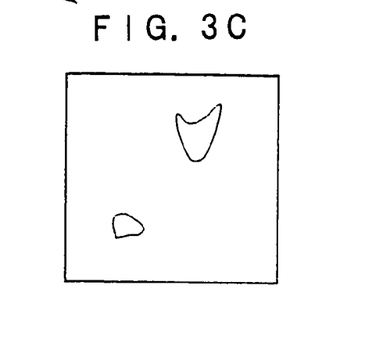

FIG. 3C shows an example of an image obtained after the extraction process. Among the portions L, M and O extracted in the process for scattered light, and the portions l and s extracted in the process for reflected light, the portion O which has been extracted only in the process for scattered light and not in the process for reflected light is removed, and the portions L-l and M-s commonly extracted in both the processes are extracted.

According to the present embodiment, a first estimation and a second estimation are carried out. In the first estimation, a defective copper portion is estimated based on the image data obtained by reading, at the position located in the oblique direction of the copper foil 26, light reflected from the copper foil 26. In the second estimation, a defective copper portion is estimated based on the image data obtained by reading, at the position located at the front of the copper foil 26, scattered light from the copper foil 26. Subsequently, a portion estimated to be a defective copper portion by both the first and second estimations is determined as the defective copper portion. Thus, a defective copper portion on the surface of the copper foil 26 can be reliably extracted with higher accuracy.

SECOND EMBODIMENT

A second embodiment will be described next. Components of the present second embodiment which are similar to those of the first embodiment are designated by the same reference numerals, and detailed description thereof will be omitted.

Figure 7:
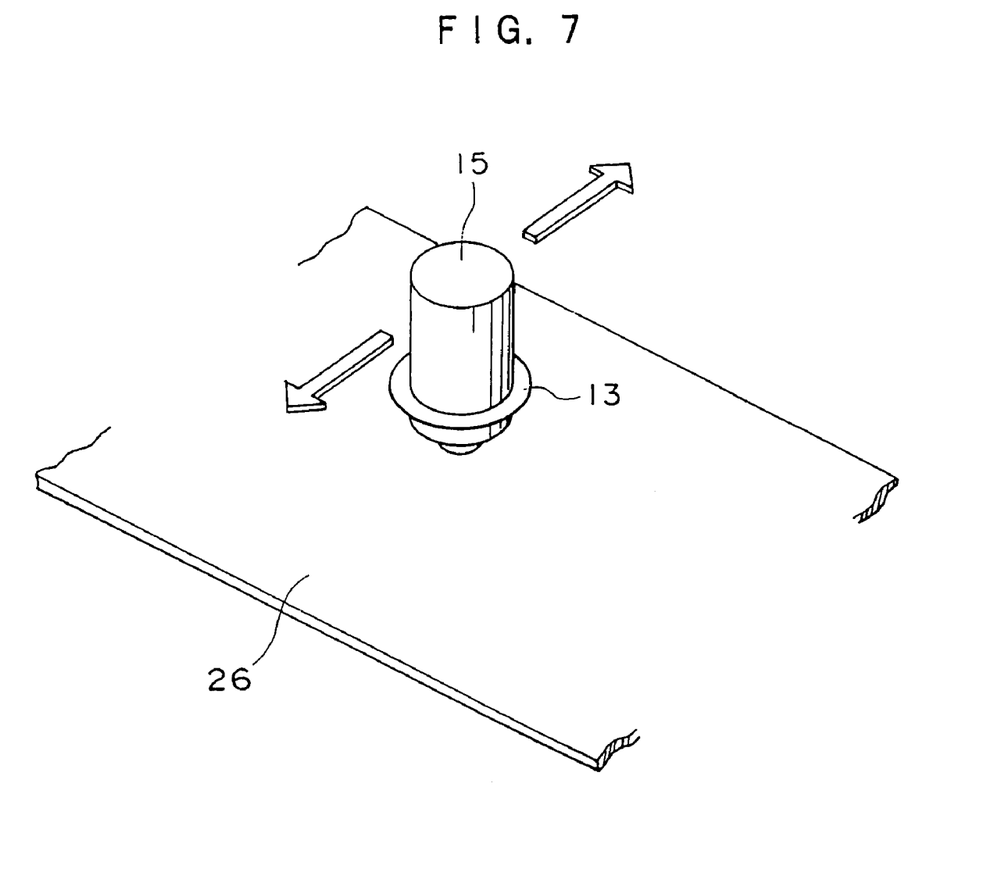
FIG. 7 is a view showing the positions of a high-resolution CCD camera and copper foil.
Figure 8:
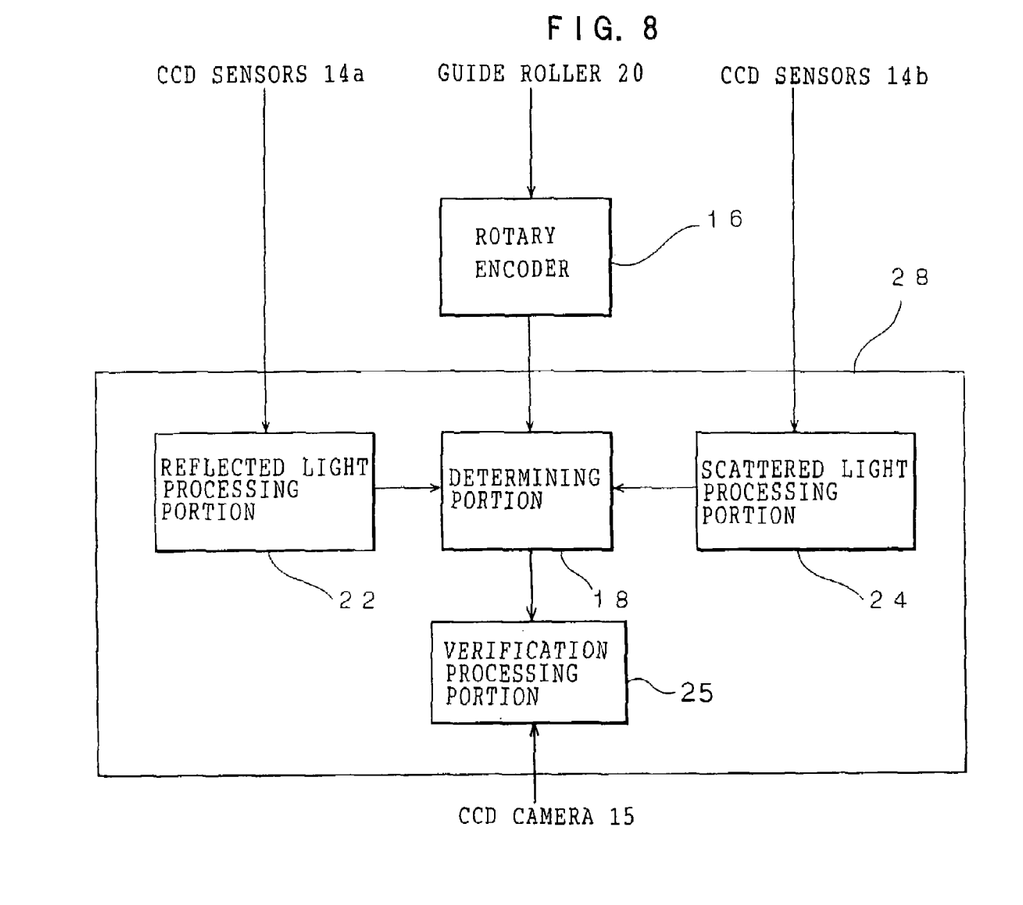
FIG. 8 is a schematic block diagram of a signal processing section according to a second embodiment.

A copper foil inspection apparatus 11 according to the present embodiment includes all the components of the copper foil inspection apparatus 10 according to the first embodiment shown in FIG. 1. Further, as shown in FIG. 7, a CCD camera 15 having resolution higher than that of the CCD sensors used in the first embodiment, and a light source 13 are disposed downstream from the copper foil surface inspection positions of the first embodiment in the direction in which the copper foil 26 is moved. Furthermore, as shown in FIG. 8, the determining portion 18 is connected to a verification processing portion 25, which in turn is connected to the CCD camera 15. The CCD camera 15 is disposed so as to be movable in the width W direction of the copper foil 26 and pick up an image of the surface of the copper foil 26 in an orientation perpendicular thereto. The light source 13 which is ring-shaped and irradiates the copper foil 26 with light is disposed at the periphery of the CCD camera 15. Further, the CCD camera 15 is also connected to the determining portion 18.

After a defective copper portion is extracted in the same way as in the first embodiment, the determining portion 18 transmits information on the position of the extracted defective portion (hereinafter referred to as the "assumed defective portion") to an unillustrated driving portion of the CCD camera 15, such that the CCD camera 15 is moved to a position at which the CCD camera 15 can pick up an image of the assumed defective portion. The light source 13 emits light when the assumed defective portion is moved and disposed under the light source 13, and the CCD camera 15 picks up an image of the surface of the assumed defective portion. The image thus picked up is transmitted to the verification processing portion 25, where a verification process is performed in accordance with a flowchart shown in FIG. 9.

Figure 9:
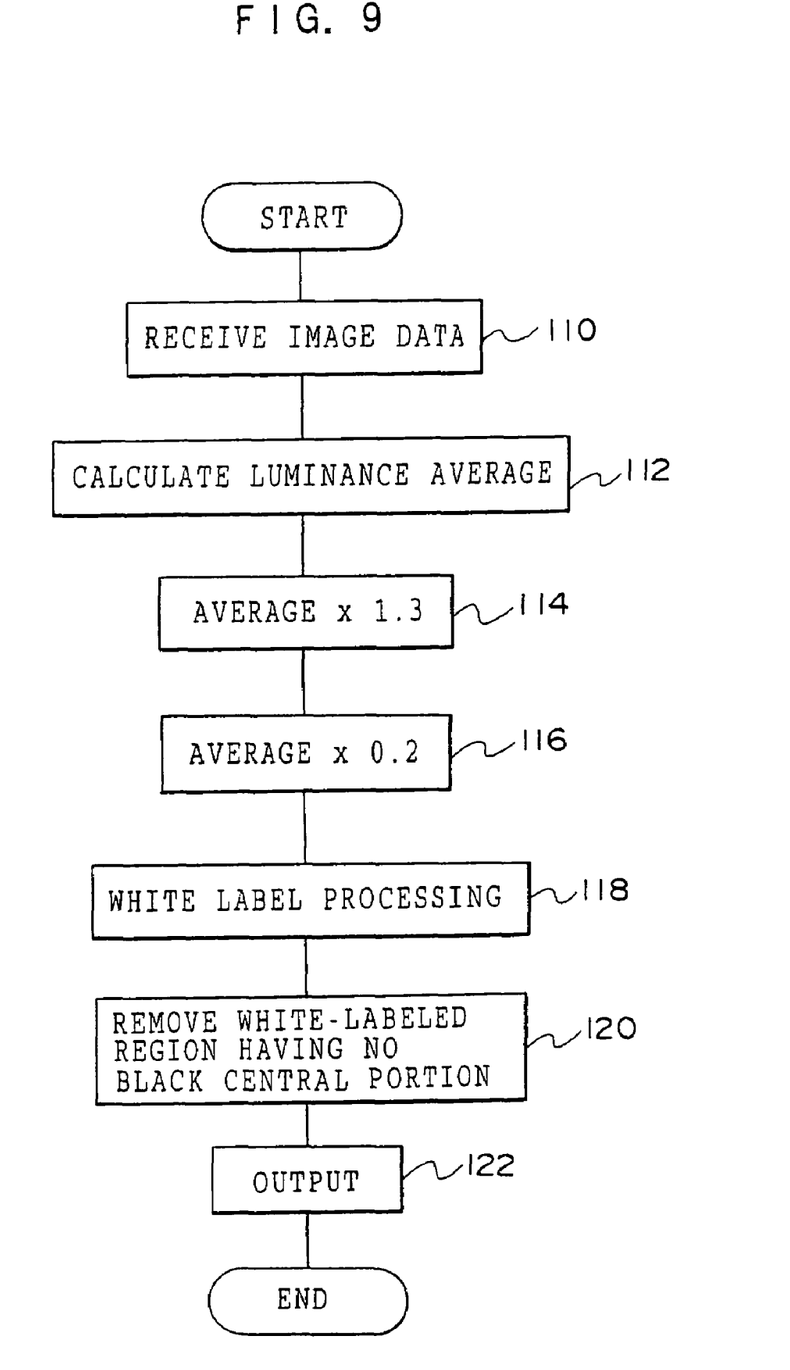
FIG. 9 is a flowchart of a verification process.

The image is received in step 110, and a luminance average of the received image is calculated in step 112. The image which has been picked up is characterized in that, for example, the defective copper portion has a black central portion and a white portion surrounding the black central portion. Thus, in step 114, a luminance threshold for a portion surrounding a portion to be extracted as a defective portion is calculated by multiplying the luminance average by 1.3, and, in step 116, a luminance threshold for the central portion of the portion to be extracted as a defective portion is calculated by multiplying the luminance average by 0.2. In step 118, the white label processing is carried out for each region formed by pixels of luminance larger than the value obtained by multiplying the luminance average by 1.3. In step 120, only a white-labeled region having a pixel of luminance smaller than the value obtained by multiplying the luminance average by 0.2 is extracted from among white-labeled regions, and other white-labeled regions are removed. Subsequently, the image which has been subjected to the white label processing is outputted in step 122, and the process ends. A white-labeled region of the output image can be determined as a defective copper portion.

According to the present embodiment, since the defective copper portion which is previously extracted is further verified by the CCD camera of higher resolution, defective copper portions can be extracted with higher accuracy. Moreover, the expensive, high-resolution CCD camera picks up an image of only a portion which is previously determined as a defective portion based on the image picked up. Thus, an image pickup range can be limited, and a defect of the copper foil can be effectively detected.

While a defective copper portion of the surface of a copper foil is extracted in the present embodiment, the present invention is not limited thereto. An image of the surface of a moving, sheet-like object to be inspected is picked up at an upstream side by a low-resolution CCD camera, and an assumed defective portion is detected based on the pickup image. Thereafter, an image of the assumed defective portion detected is further picked up at a downstream side by a high-resolution CCD camera. When it is determined that a defect exists based on the pickup image, the determination can be made that a defect is present in the detected portion. In addition to the copper foil, examples of the sheet-like object to be inspected include paper and CSP, and the present invention can be applied to these objects.

The invention claimed is:

1. A copper foil inspection apparatus comprising:
   a light source for irradiating a surface of copper foil with light;
   first light-receiving means for receiving specular light from the copper foil surface;
   second light-receiving means for receiving scattered light from the copper foil surface; and a determining portion which, when an amount of light received from a predetermined region of the copper foil surface by the first light-receiving means is no less than a first threshold and an amount of light received from the predetermined region by the second light-receiving means is no more than a second threshold which is smaller than the first threshold, determines that the predetermined region is a defective copper portion.

2. The copper foil inspection apparatus of claim 1, wherein the determining portion determines that the predetermined region is a defective copper portion when the predetermined region includes an area, from which an amount of light received by the first light-receiving means is no less than a third threshold which is larger than the first threshold.

3. The copper foil inspection apparatus of claim 1, wherein the determining portion determines that the predetermined region is a defective copper portion when the size of the predetermined region is no less than a predetermined size.

4. The copper foil inspection apparatus of claim 1, wherein the second light-receiving means receives scattered light from the front of a surface to be inspected.

5. The copper foil inspection apparatus of claim 1, further comprising third light-receiving means for receiving light reflected from the predetermined region which has been determined to be a defective copper portion, the third light-receiving means having a resolution higher than that of the first and second light-receiving means, wherein the determining portion further distinguishes the presence or absence of the defective copper portion based on the amount of light received by the third light-receiving means, and determines that the predetermined region is the defective copper portion when the determining portion distinguishes the presence of the defective copper portion.

6. A copper foil inspection process comprising:
irradiating a surface of a copper foil with light;
receiving specular light from the copper foil surface by first light-receiving means;
receiving scattered light from the copper foil surface by second light-receiving means;
determining, when an amount of light received from a predetermined region of the copper foil surface by the first light-receiving means is no less than a first threshold and an amount of light received from the predetermined region by the second light-receiving means is no more than a second threshold which is smaller than the first threshold, that the predetermined region is a defective copper portion; and
outputting a signal identifying the predetermined region.

7. The copper foil inspection process of claim 6, wherein, in the determining step, the predetermined region is determined to be a defective copper portion when the predetermined region includes an area, from which an amount of light received by the first light-receiving means is no less than a third threshold which is larger than the first threshold.

8. The copper foil inspection process of claim 6, wherein, in the determining step, the predetermined region is determined to be a defective copper portion when the size of the predetermined region is no less than a predetermined size.

9. The copper foil inspection process of claim 6, wherein the second light-receiving means receives scattered light from the front of a surface to be inspected.

10. The copper foil inspection process of claim 9, further comprising receiving light reflected from the predetermined region which has been determined to be a defective copper portion, by third light-receiving means having a resolution higher than that of the first and second light-receiving means, wherein, in the determining step, the presence or absence of the defective copper portion is distinguished based on the amount of light received by the third light-receiving means, and the predetermined region is determined to be the defective copper portion when the presence of the defective copper portion is distinguished.

* * * * *